(12) United States Patent
Takagi et al.

(10) Patent No.: US 8,287,917 B2
(45) Date of Patent: Oct. 16, 2012

(54) HYDROGEL PARTICLE

(75) Inventors: Michiya Takagi, Wakayama (JP);
Kazuo Matsuyama, Wakayama (JP);
Koji Mine, Wakayama (JP); Hideaki Kubo, Wakayama (JP)

(73) Assignee: Kao Corporation, Tokyo (JP)

( * ) Notice: Subject to any disclaimer, the term of this patent is extended or adjusted under 35 U.S.C. 154(b) by 347 days.

(21) Appl. No.: 12/096,497

(22) PCT Filed: Dec. 5, 2006

(86) PCT No.: PCT/JP2006/324217
§ 371 (c)(1),
(2), (4) Date: Jul. 23, 2008

(87) PCT Pub. No.: WO2007/066635
PCT Pub. Date: Jun. 14, 2007

(65) Prior Publication Data
US 2010/0015186 A1    Jan. 21, 2010

(30) Foreign Application Priority Data
Dec. 7, 2005    (JP) .................................. 2005-353636

(51) Int. Cl.
*A61K 8/27* (2006.01)
*A61K 8/04* (2006.01)
*A61K 8/34* (2006.01)
*A61K 8/92* (2006.01)
*A61Q 1/02* (2006.01)
*A61Q 17/04* (2006.01)

(52) U.S. Cl. ........................... 424/642; 424/59; 424/401

(58) Field of Classification Search .................. None
See application file for complete search history.

(56) References Cited

U.S. PATENT DOCUMENTS 6,036,945 A * 3/2000 Deblasi et al. .................. 424/59
2002/0034525 A1 * 3/2002 Sakai et al. .................... 424/401

FOREIGN PATENT DOCUMENTS

| JP | 2001 187710 | 7/2001 |
| JP | 2001-187710 | 7/2001 |
| JP | 2002 20227 | 1/2002 |
| JP | 2002 20228 | 1/2002 |
| JP | 2002 58990 | 2/2002 |
| JP | 2002 159838 | 6/2002 |
| JP | 2002-159838 | 6/2002 |

OTHER PUBLICATIONS

Mitchnick MA, Fairhurst D, and Pinnell SR. Microfine zinc oxide (Z-Cote) as a photostable UVA/UVB sunblock agent. J. Am. Acad. Dermatol. (1999) 40:85-90.*
CAS (STN) Registry No. 661-19-8 (Nov. 16, 1984).*
Agrawal et al. Microcrystalline Waxes: Investigations on the Structure of Waxes by Proton Nuclear Magnetic Resonance Spectroscopy. J. Chem. Tech. Biotechnol. 1981;31:693-696.*
U.S. Appl. No. 12/374,099, filed Jan. 16, 2009, Takagi, et al.
U.S. Appl. No. 13/131,770, filed May 27, 2011, Takagi, et al.

* cited by examiner

*Primary Examiner* — David J Blanchard
*Assistant Examiner* — Peter Anthopolos
(74) *Attorney, Agent, or Firm* — Oblon, Spivak, McClelland, Maier & Neustadt, L.L.P.

(57) ABSTRACT

A hydrogel particle contains a continuous phase portion of non-crosslinked hydrogel and a large number of disperse phase portions dispersed in the continuous phase portion. Each of the large number of disperse phase portions is a solid phase containing an oil component and particles of zinc oxide dispersed therein.

10 Claims, No Drawings

HYDROGEL PARTICLE

CROSS REFERENCES TO RELATED APPLICATIONS

This application is a 371 of International Patent Application No. PCT/JP2006/324217, filed on Dec. 5, 2006, and claims priority to Japanese Patent Application No. 2005-353636, filed on Dec. 7, 2005.

TECHNICAL FIELD

The present invention relates to a hydrogel particle applicable to, for example, cosmetic products, quasi drugs, etc.

BACKGROUND ART

A known hydrogel particle containing an oil component is a hydrogel particle formed by the continuous phase portion of non-crosslinked hydrogel and the disperse phase portions containing an oil component (see, for example, Patent Document 1). The hydrogel particle is characterized in that, when used in a cosmetic product, or the like, the particle can be smoothly crushed by fingers at the time of application over the human skin, or the like. Further, it exhibits excellent spreadability with no residue and excellent crushability.

Although a hydrogel particle containing a pigment as a colorant in the disperse phase portions has been known, there has not been a hydrogel particle containing zinc oxide particles which have UV-shielding property in the disperse phase portions.

Zinc oxide is naturally soluble in water in a small amount. Such solubility causes various disadvantages in designing cosmetic products. For example, in the case of a conventional sunscreen cosmetic product containing ultrafine powder of zinc oxide, it is difficult to increase the water content to 50 mass % or more. Thus, most of the emulsified products are water-in-oil (W/O) products. Meanwhile, ultrafine powder of zinc oxide can react with other ingredients, such as a variety of oils, perfumes, colorants, organic UV absorbers, water-soluble polymer, etc., to cause an increase or decrease in viscosity of the cosmetic product, to produce a stench, or to cause discoloration. Because of such problems, the use of ultrafine powder of zinc oxide in cosmetic products is restricted with limited applicability.

Patent Document 1: Japanese Laid-Open Patent Publication No. 2002-159838 (Japanese Patent No. 3483543)

DISCLOSURE OF INVENTION

An objective of the present invention is to provide a hydrogel particle wherein particles of zinc oxide are stably present in the disperse phase portions.

To achieve the above objective, the present invention provides a hydrogel particle including a continuous phase portion of non-crosslinked hydrogel and a large number of disperse phase portions dispersed in the continuous phase portion, wherein each of the large number of disperse phase portions is solid phase containing an oil component and contains particles of zinc oxide dispersed therein.

According to the present invention, the disperse phase portions containing zinc oxide particles dispersed therein are solid phase and, therefore, the zinc oxide particles are fixedly and stably present in the disperse phase portions. Thus, in the case where the hydrogel particles of the present invention are applied to a cosmetic product or the like, such a disadvantage that zinc oxide particles leak out of the hydrogel particles and react with other ingredients can be avoided.

BEST MODE FOR CARRYING OUT THE INVENTION

Hereinafter, an embodiment of the present invention is described in detail.

A hydrogel particle of this embodiment includes a continuous phase portion of non-crosslinked hydrogel and a large number of disperse phase portions dispersed in the continuous phase portion. Each of the large number of disperse phase portions is solid phase containing an oil component and contains particles of zinc oxide dispersed therein. The zinc oxide particles have UV-shielding property.

In such a hydrogel particle, the disperse phase portions containing zinc oxide particles dispersed therein are solid phase and, therefore, the zinc oxide particles are fixedly and stably present in the disperse phase portions. Thus, the hydrogel particles are applicable to a formulation which is unstable to zinc ion and which has conventionally been difficult to contain zinc oxide. Specifically, for example, in the case where the hydrogel particles are applied to a cosmetic product or the like, such a disadvantage that zinc oxide particles leak out of the hydrogel particles and react with other ingredients can be avoided.

The term "hydrogel particle(s)" as referred to in this application means one or more particles of hydrogel in which an oil component is dispersed. It should be noted that the concept of the "hydrogel particle" does not include a capsule composed of concentric outer layer (shell) and inner layer (core). The term "hydrogel" as referred to in this application means gel formed from a gel source using water as solvent.

In view of the appearance and productivity, the volume-average particle diameter of the hydrogel particles is preferably 10 to 10000 μm, more preferably 15 to 5000 μm, and still more preferably 20 to 3000 μm. The volume-average particle diameter of hydrogel particles can be measured by photographic observation for the particle diameter of 500 μm or more, or by a laser diffraction scattering method using a laser diffraction/scattering particle size distribution analyzer for the particle diameter of less than 500 μm.

The shape of the hydrogel particle is not limited to anything particular but is preferably the shape of a body of revolution which is composed of a curved surface. The "body of revolution which is composed of a curved surface" refers to a three-dimensional body defined by rotating a closed plane formed by a continuous curve and a virtual axis, but does not include a three-dimensional body having a flat surface, such as a triangular pyramid, circular cylinder, etc. In view of beautiful appearance, the shape of the hydrogel particle is more preferably spherical.

The hydrogel particle of this embodiment includes a continuous phase portion of non-crosslinked hydrogel.

In view of preventing collapse during washing of the hydrogel particles and blending of the hydrogel particles into cosmetic products or the like, the content of the continuous phase portion in the hydrogel particle is preferably 30 to 99 mass %, and more preferably, 30 to 80 mass %.

The term "non-crosslinked hydrogel" as referred to in this application means a product of gelation caused by the heat-reversibility of sol-gel as is the case with agar used as the gel source. For example, the dissolution temperature of agars in water is generally 75° C. or higher. Commonly-employed agars are dissolved in water at 75 to 90° C. The gelation temperature of agar when cooled after dissolved in water is 30 to 45° C.

The continuous phase portion is non-crosslinked hydrogel which contains a gel source and water.

Examples of the gel source include agar, carageenan, and gelatin. The gel source can be formed by one of or a mixture of two or more of these examples. It should be noted that agar is preferable among these examples. In view of the feel of a cosmetic product or the like containing the hydrogel particles when used, the jelly strength of agar is preferably 147 kPa (1500 g/cm$^2$) or lower, and more preferably 19.6 kPa (200 g/cm$^2$) to 127 kPa (1300 g/cm$^2$). The jelly strength can be determined using the Nikkansuishiki method, which is specifically as follows. First, a 1.5 mass % aqueous solution of the gel source is prepared. The aqueous solution is kept at 20° C. for 15 hours to obtain a gel product. The gel product is subjected to a load applied by a Nikkansuishiki jelly strength measuring apparatus (manufactured by Kabushiki Kaisha KIYA SEISAKUSHO). The gel strength is represented by the maximum mass (g) per 1 cm$^2$ surface area when the gel product withstands the load for 20 seconds at 20° C.

In view of the pleasant feel of a cosmetic product or the like containing the hydrogel particles when used and in view of preventing collapse during washing of the hydrogel particles and blending of the hydrogel particles into cosmetic products or the like, the content of the gel source in the continuous phase portion is preferably 0.1 to 8.0 mass %, more preferably 0.3 to 7.0 mass %, still more preferably 0.4 to 6.0 mass %, and especially preferably 0.5 to 5.0 mass %. In view of the pleasant feel of a cosmetic product or the like containing the hydrogel particles when used and in view of preventing collapse during washing of the hydrogel particles and blending of the hydrogel particles into cosmetic products or the like, the content of the gel source in the hydrogel particle is preferably 0.1 to 8.0 mass %, more preferably 0.3 to 7.0 mass %, still more preferably 0.4 to 6.0 mass %, and especially preferably 0.5 to 5.0 mass %.

The hydrogel particle of this embodiment includes a large number of disperse phase portions dispersed in the continuous phase portion.

In view of preventing collapse during washing of the hydrogel particles and blending of the hydrogel particles into cosmetic products or the like, the content of the disperse phase portions in the hydrogel particle is preferably 1 to 70 mass %, more preferably 7.5 to 70 mass %, still more preferably 10 to 70 mass %, and especially preferably 20 to 60 mass %.

The volume-average particle diameter of the disperse phase portions is preferably 10% or less of the volume-average particle diameter of the hydrogel particles. Specifically, in view of smooth spreadability over the human skin of a cosmetic product or the like containing the hydrogel particles, the volume-average particle diameter of the disperse phase portions is preferably 100 μm or less, more preferably 50 μm or less, and especially preferably 20 μm or less. In view of the compatibility with the human skin of a cosmetic product or the like containing the hydrogel particles, the volume-average particle diameter of the disperse phase portions is preferably 0.01 μm or more, more preferably 4 μm or more, still more preferably 5 μm or more, and especially preferably 10 μm or more. Thus, the volume-average particle diameter of the disperse phase portions is preferably 0.01 to 100 μm, more preferably 4 to 100 μm, still more preferably 5 to 50 μm, and especially preferably 5 to 20 μm. The volume-average particle diameter of the disperse phase portions can be measured with a dispersion before particle formation using a laser diffraction/scattering particle size distribution analyzer (for example, LA-910 manufactured by HORIBA, Ltd.).

In the hydrogel particle of this embodiment, each disperse phase portion includes an oil component.

In view of the good feel of a cosmetic product or the like containing the hydrogel particles when used, the total content of the oil component in all the disperse phase portions is preferably 1 to 99 mass %, and more preferably 50 to 99 mass %.

In view of the good feel of a cosmetic product or the like containing the hydrogel particles when used and in view of preventing collapse during washing of the hydrogel particles and blending of the hydrogel particles into cosmetic products or the like, the total content of the oil component in the hydrogel particle is preferably 0.01 to 60 mass %, more preferably 7.5 to 50 mass %, and still more preferably 10 to 40 mass %.

In view of suppressing leakage of the oil component from the hydrogel particles when stored at a high temperature, the melting point of the disperse phase portions is preferably 35° C. or higher, more preferably 40 to 90° C., still more preferably 45 to 90° C., and especially preferably 50 to 80° C. The melting point of the oil component can be measured by DSC (Differential Scanning Calorimetry). The melting points of solid oil and liquid oil (described later) can also be measured by DSC.

The oil component may contain solid oil and liquid oil.

In view of suppressing leakage of the oil component from the hydrogel particles and in view of smooth spreadability over the human skin of a cosmetic product or the like containing the hydrogel particles, the content of solid oil in the oil component is preferably 1 to 80 mass %, more preferably 6 to 80 mass %, still more preferably 10 to 70 mass %, and especially preferably 19 to 50 mass %.

In view of suppressing leakage of the oil component from the hydrogel particles, the melting point of the solid oil is preferably 35° C. or higher, more preferably 40 to 120° C., still more preferably 50 to 90° C., and especially preferably 50 to 80° C.

Examples of the solid oil include solid ceramide, solid sphingolipid, solid paraffin, solid higher alcohol, vaseline, solid silicone, solid perfumes, and other types of solid oils. The solid oil can be formed by one of these examples or by two or more of these examples. Among these examples, in view of suppressing dissolution of zinc oxide particles in water, solid higher alcohol is preferable, and solid higher alcohol with 14 to 22 carbon atoms is especially preferable. In the case where the solid oil is formed by solid higher alcohol, concomitantly using solid paraffin is preferable, and concomitantly using solid isoparaffin is more preferable, in view of suppressing dissolution of zinc oxide particles in water.

In view of the good dispersion stability and suppression of leakage of the oil component from the hydrogel particles, a preferable example of the solid ceramide is N-(2-hydroxy-3-hexadeciroxypropyl)-N-2-hydroxyethylhexadecanamid.

Examples of the solid higher alcohol include myristyl alcohol, cetyl alcohol, cetostearyl alcohol, stearyl alcohol, 2-octyldodecanol, arachidyl alcohol, and behenyl alcohol. The oil component may include only one of these examples or may include two or more of these examples. Among these examples, in view of suppressing dissolution of zinc oxide particles in water, cetyl alcohol, stearyl alcohol, arachidyl alcohol, and behenyl alcohol are preferable. More preferably, two or more of these higher alcohols are used together.

Examples of the solid paraffin include paraffin waxes and microcrystalline waxes listed in JIS K 2235, ceresine, soft solders, and paraffins listed in The Japanese Pharmacopoeia. The oil component may include only one of these examples or may include two or more of these examples.

Examples of the solid silicone include alkyl-denatured silicone and polymer-silicone-denatured and alkyl-denatured acrylic resin.

Examples of the other types of solid oils include hardened oil and higher fatty acid. Examples of the hardened oil include hardened oil made from coconut oil, palm oil, or tallow. Examples of the higher fatty acid include palmitic acid, behenic acid, and stearic acid.

Examples of the solid perfumes include menthol and cedrol.

In view of suppressing leakage of the oil component from the hydrogel particles and in view of smooth spreadability over the human skin of a cosmetic product or the like containing the hydrogel particles, the content of liquid oil in the oil component is preferably 50 to 99 mass %, more preferably 20 to 94 mass %, still more preferably 30 to 90 mass %, and especially preferably 50 to 81 mass %.

The "liquid oil" refers to one having a melting point lower than 35° C., and examples thereof include liquid skin protecting agents, liquid perfumes, and other types of liquid oils. It should be noted that the liquid oil preferably contains a liquid skin protecting agent in view of skin protection.

The liquid skin protecting agent is a constituent for softening or smoothing the skin for the purpose of preventing surface roughening. Examples of the liquid skin protecting agent include: liquid fats and oils, such as liquid paraffin, liquid ester oil, liquid higher alcohol, liquid squalan, liquid glyceride, and the like; liquid ceramides, such as cetyloxypropyl glyceryl methoxypropylmyristamide, and the like; and liquid sphingolipid, such as 1-(2-hydroxyethylamino)-3-isostearyloxy-2-propanol, and the like. The oil component may include only one of these examples or may include two or more of these examples.

Examples of the other types of liquid oils include liquid hydrocarbon oils, liquid vegetable oils, liquid fatty acids; liquid fats and oils, such as liquid ethylene glycol di-fatty acid ester (fatty acid having 12 to 36 carbon atoms), liquid dialkyl ether (with 12 to 36 carbon atoms), and the like; and liquid silicones. The other types of liquid oils may be volatile or nonvolatile. Examples of the liquid vegetable oils include soybean oil, coconut oil, palm kernel oil, linseed oil, cottonseed oil, colza oil, tung oil, and castor oil. Examples of the liquid fatty acids include oleic acid and caprylic acid. The liquid silicones may be any polymer having a silanol structure. Examples of the liquid silicones include methylpolysiloxane, methylphenylsiloxane, octamethylcyclotetrasiloxane, decamethylcyclopentasiloxane, methylhydrogenpolysiloxane, highpolymeric-methyl polysiloxane, silicone resins, amino-denatured silicones, and alkyl-denatured silicones. Other examples of the liquid oils include organic UV absorbers, such as 2-Ethylhexyl 4-Methoxycinnamate, 4-Methoxy-4'-tert-butyldibenzoylmethane, 2-Ethylhexyl dimethoxybenzylidene dioxoimidazolidine propionate, etc. The oil component may include only one of these examples or may include two or more of these examples.

The liquid perfumes may be conventionally-employed, commonly-known perfumes.

In the hydrogel particle of this embodiment, each disperse phase portion is solid phase.

The term "solid disperse phase portion" as referred to in this application means a phase having the compression breaking stress of 2 kPa or more when measured for the composition constituting the disperse phase portion using a digital force gauge (FGS-0.2R manufactured by NIDEC-SHIMPO CORPORATION (minimum measurement load: 2 mN)) attached to a test stand (FGS-50V-L manufactured by NIDEC-SHIMPO CORPORATION). The term "compression breaking stress" as referred to herein means the local maximum value of the load curve. The gauge head is a flat adapter, and the lowering speed of the gauge head is 10 mm/min. The measurement temperature is 25° C.

In the hydrogel particle of this embodiment, each disperse phase portion contains zinc oxide particles dispersed therein. Zinc oxide particles have UV-shielding property.

In view of UV-shielding property, the total content of zinc oxide particles in all the disperse phase portions is preferably 5 to 60 mass %, more preferably 10 to 60 mass %, and still more preferably 10 to 50 mass %. In view of UV-shielding property, the total content of zinc oxide particles in the hydrogel particles is preferably 0.1 to 40 mass %, more preferably 1 to 40 mass %, and still more preferably 1 to 30 mass %.

As for the zinc oxide particles used herein, the average particle diameter of primary particles is 0.001 to 0.1 µm. The zinc oxide particles have UV-shielding property. The phrase "having UV-shielding property" means having the effect of absorbing or scattering ultraviolet light in the wavelength range of 280 to 400 nm, especially UVB and UVAII in the wavelength range of 280 to 340 nm.

In view of the feel of a product when applied, the average particle diameter of primary particles of the zinc oxide particles is preferably 0.001 µm or more, more preferably 0.005 µm or more, and especially preferably 0.01 µm or more. In view of transparency of a cosmetic product when applied, the average particle diameter of primary particles of the zinc oxide particles is preferably 0.1 µm or less, more preferably 0.08 µm or less, and especially preferably 0.06 µm or less. The average particle diameter is represented by the number average value of the particle diameter measured by electron micrograph observation unless otherwise specified.

The continuous phase portion may contain, in addition to the gel source of non-crosslinked hydrogel and water, a water-soluble organic compound, such as a saccharide, polyhydric alcohol, water-soluble polymer compound, water-soluble perfume, or the like, which are described in Japanese Laid-Open Patent Publication No. 2000-126586.

Each of the continuous phase portion and disperse phase portions may contain other components, such as colorants, preservatives, etc.

Examples of the colorants include pigments and dyes.

Examples of the pigments include inorganic pigments, such as carbon black, iron red, titanium oxide, etc., and organic pigments, such as tar pigment, etc.

Examples of the dyes include solvent dye, vat dye, and color lake.

Examples of the preservatives include paraoxymethylbenzoate, isopropylmethylphenol, ethanol, phenoxyethanol, dehydroacetic acid, and salts thereof.

Each of the continuous phase portion and disperse phase portions may contain other components applicable to cosmetic products, drugs, quasi drugs, and the like, such as humectants, antiperspirants, antimicrobial agents, bactericides, powders, etc.

Each of the continuous phase portion and disperse phase portions may contain fine particles of titanium oxide, which have UV-shielding property.

The hydrogel particle of this embodiment may includes, in addition to the continuous phase portion and the disperse phase portions, an oily disperse phase portion which contains oil, such as organic UV absorbers, feel regulators, etc., but which does not contain zinc oxide particles.

Next, a method for producing the hydrogel particles of this embodiment is described.

First, for an aqueous component, a gel source is mixed with ion-exchanged water, and the mixture is heated to a temperature equal to or higher than the melting point of the gel source so as to sufficiently dissolve the gel source. Meanwhile, constituents for the oil component are mixed and dissolved by heating.

Then, the aqueous component and the oil component are mixed at a temperature equal to or higher than the gelation temperature to prepare an oil-in-water dispersion. The method for preparing the oil-in-water dispersion is not limited to any particular method. The preparation of the oil-in-water dispersion can be carried out using a known technique with any of various stirrers and dispersers.

In view of the stability of the oil-in-water dispersion, adding an emulsifying/dispersing agent to the aqueous component and/or oil component is preferable. Adding an emulsifying/dispersing agent to the aqueous component is especially preferable.

In view of the good feel of a cosmetic product or the like containing the hydrogel particles when used and in view of the stability of the oil-in-water dispersion and the leakage prevention of the oil components dispersed in the hydrogel particles, the amount of the emulsifying/dispersing agent added is preferably 0.001 to 20 parts by mass, more preferably 0.01 to 5 parts by mass, where the total amount of the oil-in-water dispersion is 100 parts by mass.

Examples of the emulsifying/dispersing agent include polymer emulsifying/dispersing agents, nonionic surfactants, anionic surfactants, cationic surfactants, and amphoteric surfactants. Only one of these examples or two or more of these examples may be included.

Among the emulsifying/dispersing agents, in view of smooth spreadability over the human skin of a cosmetic product or the like containing the hydrogel particles and in view of good handleability during washing of the hydrogel particles and blending of the hydrogel particles into cosmetic products or the like, concomitantly using a nonionic surfactant, anionic surfactant, cationic surfactant, or amphoteric surfactant with a polymer emulsifying/dispersing agent is preferable. More preferably, a nonionic surfactant and a polymer emulsifying/dispersing agent are concomitantly used. Still more preferably, a polymer emulsifying/dispersing agent is solely used. In the case where a polymer emulsifying/dispersing agent is used as the emulsifying/dispersing agent, addition of a surfactant can be reduced or eliminated. Therefore, stickiness of a cosmetic product or the like containing the hydrogel particles which may be caused by a surfactant when applied on the human skin can be reduced.

Examples of the polymer emulsifying/dispersing agent include synthetic polymer compounds, such as a copolymer of acrylic acid and alkyl methacrylate, a composite formed by a reaction of an amphoteric polymer and a higher fatty acid described in Japanese Laid-Open Patent Publication No. 7-100356, water-soluble amphiphilic polymer electrolytes described in Japanese Laid-Open Patent Publications Nos. 8-252447 and 9-141079, water-soluble crosslinked amphiphilic polymer electrolytes described in Japanese Laid-Open Patent Publications Nos. 9-141080 and 9-141081, acrylic acid copolymer described in Japanese Laid-Open Patent Publication No. 10-53625, polysaccharide derivatives described in the Gazette of Japanese Patent No. 3329689 and Japanese Laid-Open Patent Publications Nos. 10-330401 and 11-106401, polyvinyl pyrrolidone, polyvinyl alcohol and a derivative thereof, polyacrylamide, an adduct of alkylphenol-formaldehyde condensation product and ethyleneoxide, etc., and naturally-occurring polymer compounds, such as Guar gum, Karaya gum, Tragacanth gum, Arabic gum, Arabinogalactan, casein, etc. Only one of these examples or two or more of these examples may be included.

Among the polymer emulsifying/dispersing agents, in view of reduction in stickiness of a cosmetic product or the like containing the hydrogel particles when applied on the human skin, a copolymer of acrylic acid and alkyl methacrylate (e.g., PEMULEN manufactured by Nikko Chemicals Co., Ltd.), polyvinyl alcohol (e.g., GOHSENOL manufactured by Nippon Synthetic Chemical Industry Co., Ltd.), and polysaccharide derivatives described in the Gazette of Japanese Patent No. 3329689 are preferably used. More preferably, polyvinyl alcohol and a polysaccharide derivative described in the Gazette of Japanese Patent No. 3329689 are concomitantly used.

In view of improving emulsifiability and dispersibility, a neutralized polymer emulsifying/dispersing agent may be added. Alternatively, potassium hydroxide, sodium hydroxide, or the like, may be added to the aqueous component and/or oil component before or after dispersed, such that the polymer emulsifying/dispersing agent is neutralized. The value of pH after neutralization is normally 4 to 8, and preferably 6 to 7.

Examples of the anionic surfactants include sodium lauryl sulfate, sodium stearate, and polyoxyethylenelauryl ether sodium phosphate.

Examples of the cationic surfactants include lauryltrimethylammoniumchloride, stearylamineacetate, and stearylamine acid.

In view of leakage prevention of the oil components from produced hydrogel particles, the nonionic surfactant preferably has a HLB value of 10 or less, more preferably 8 or less, still more preferably 5 or less, and especially preferably 3 or less. HLB value can be determined based on a formula described in *Techniques of Emulsification and Solubilization* published by Kougakutosho Ltd. (1984-5-20), pp. 8-12.

Among such nonionic surfactants, in view of small skin irritation caused by a cosmetic product or the like containing produced hydrogel particles, sorbitan fatty acid ester, polyoxyethylene sorbitan fatty acid ester, and polyoxyethylene sorbitol fatty acid ester are preferably used. More preferably, sorbitan monostearate is used. In view of leakage prevention of the oil components from produced hydrogel particles, the melting point of the nonionic surfactant used is preferably 35° C. or higher, more preferably 40 to 90° C., still more preferably 50 to 90° C., and especially preferably 60 to 80° C.

Examples of the amphoteric surfactants include alkydimethylaminoacetic acid betaine and lecithin.

After the preparation of the oil-in-water dispersion, hydrogel particles are produced from the oil-in-water dispersion using a commonly-employed dropping, spraying, or stirring method. It should be noted that, in view of suppressing leakage of the oil component from the hydrogel particles, a dropping or spraying method is preferably used rather than a stirring method.

The dropping method utilizes such a property that the oil-in-water dispersion ejected through an orifice forms droplets by the surface or interfacial tension. The droplets are cooled in a gas phase (e.g., air) or liquid phase to solidify into hydrogel particles. In view of producing hydrogel particles of uniform particle diameter, the oil-in-water dispersion ejected through the orifice is preferably vibrated.

The spraying method uses a spray nozzle through which the dispersion is sprayed into a gas phase such that droplets of the dispersion are formed by the surface tension. The droplets are cooled in the gas phase to solidify into hydrogel particles.

In the stirring method, the oil-in-water dispersion is poured into a solution which has the property of being substantially unmixable with the oil-in-water dispersion and which is regulated to a temperature equal to or higher than the gelation temperature. The solution is stirred such that the oil-in-water dispersion is atomized by the shearing force of stirring, whereby droplets are formed by the surface tension. The droplets are cooled in a liquid which is substantially unmixable with the oil-in-water dispersion to solidify into hydrogel particles.

Whichever of the dropping method, spraying method, and stirring method is employed, the temperature of the oil-in-water dispersion when ejected, sprayed, or poured is preferably between the gelation temperature and 100° C. In view of readily producing spherical particles with beautiful appearance, the temperature of the oil-in-water dispersion is preferably higher than the gelation temperature by 10° C. or more, more preferably higher than the gelation temperature by 20° C. or more. It should be noted that the upper limit of this temperature is the boiling point of water, i.e., 100° C.

The thus-produced hydrogel particles may be processed into finer hydrogel particles by crushing or any other means as necessary.

EXAMPLES (Hydrogel Particles)
Hydrogel particles of examples 1 to 5 and comparative examples 1 and 2 described below were prepared. The details of these samples are also shown in TABLE 1.

Example 1

The oil component and aqueous component having the composition shown in TABLE 1, 500 g in total, were dissolved by heating at 80° C. and 90° C., respectively. Then, the aqueous component solution is cooled to 80° C. The oil and aqueous components are mixed and stirred at 80° C. by an anchor-type stirrer to obtain a mixture solution.

Then, the mixture solution was stirred for one minute using an emulsifier (T.K. HOMO MIXER MARK II Model 2.5 manufactured by Tokushu Kika Kogyo Kabushiki Kaisha) at 8000 rpm to prepare an oil-in-water dispersion.

The oil-in-water dispersion was regulated to 80° C. and ejected through a nozzle having a diameter of 1.2 mm at the flow rate of 10 mL/min into an oil (methyl polysiloxane manufactured by Shin-Etsu Chemical Co., Ltd. under the trade name of SILICONE KF-96A (20CS)) regulated to 10° C. After solid-liquid separation, oil surrounding the particle surface was removed to produce hydrogel particles. These hydrogel particles are referred to as Example 1.

The oily disperse phase components of Example 1 were dissolved by heating at 80° C. to prepare a disperse phase component solution. The disperse phase component solution was cooled in a petri dish to solidify, whereby a solid material of the disperse phase was produced.

Example 2

Hydrogel particles of Example 2 were prepared in the same way as Example 1 except that the solid oil was changed as shown in TABLE 1. Also, a solid material of the disperse phase of Example 2 was produced.

Example 3

Hydrogel particles of Example 3 were prepared in the same way as Example 1 except that the solid oil was changed as shown in TABLE 1. Also, a solid material of the disperse phase of Example 3 was produced.

Example 4

Hydrogel particles of Example 4 were prepared in the same way as Example 1 except that the solid oil was changed as shown in TABLE 1. Also, a solid material of the disperse phase of Example 4 was produced.

Example 5

Hydrogel particles of Example 5 were prepared in the same way as Example 1 except that the solid oil was changed as shown in TABLE 1. Also, a solid material of the disperse phase of Example 5 was produced.

Comparative Example 1

Hydrogel particles of Comparative Example 1 were prepared in the same way as Example 1 except that the solid oil was not contained. Also, a solid material of the disperse phase of Comparative Example 1 was produced.

Comparative Example 2

Hydrogel particles of Comparative Example 2 were prepared in the same way as Example 1 except that the solid oil was changed as shown in TABLE 1. Also, a solid material of the disperse phase of Comparative Example 2 was produced.

TABLE 1

| | | | | Melting Point (° C.) | Example 1 | Example 2 | Example 3 | Example 4 | Example 5 | Comparative 1 | Comparative 2 |
|---|---|---|---|---|---|---|---|---|---|---|---|
| Composition of Hydrogel Particle (mass %) | Disperse Phase | Liquid Oil | Decamethyl Cyclopentasiloxane manufactured by Shin-Etsu Chemical Co., Ltd. Trade Name: KF-995 | −40 | 5.0 | 5.0 | 5.0 | 5.0 | 5.0 | 5.0 | |
| | | | UV absorber (*1) | −25 | | | | | | | 27.5 |
| | | Solid Oil | Higher Alcohol manufactured by Kao Corporation Trade Name: KALCOL220-80 | 65 to 73 | | | 5.0 | 2.5 | 2.5 | | |
| | | | Solid Silicone manufactured by Shin-Etsu Chemical Co., Ltd. Trade Name: KP562P | 45 to 55 | 5.0 | | | | | | |
| | | | Higher Fatty Acid manufactured by Kao Corporation Trade Name: LUNAC BA | 80 | | 2.0 | | | | | |

TABLE 1-continued

| | | Melting Point (°C.) | Example 1 | Example 2 | Example 3 | Example 4 | Example 5 | Comparative 1 | Comparative 2 |
|---|---|---|---|---|---|---|---|---|---|
| | Solid Paraffin manufactured by Nikko Rica Corporation Trade Name: Ceresin #810A | 75 to 85 | | | | | 2.5 | | |
| | Solid Paraffin manufactured by Nippon Seiro Co., Ltd. Trade Name: Hi-Mic-1045 | 70 | | | | 2.5 | | | |
| | N-(2-hydroxy-3-hexadeciroxypropyl)-N-2-hydroxyethylhexadecanamid manufactured by Kao Corporation Trade Name: Sphingolipid E | 69 to 77 | | | | | | | 5.0 |
| | Zinc Oxide Fine Particle Dispersion manufactured by Shin-Etsu Chemical Co., Ltd. Trade Name: SPD-Z5 | | 25.0 | 25.0 | 25.0 | 25.0 | 25.0 | 25.0 | |
| | Zinc Oxide Fine Particles | | | | | | | | 5.0 |
| | Titanium Oxide Fine Particles | | | | | | | | 5.0 |
| Continuous Phase | Agar UP-16 | | 1.0 | 1.0 | 1.0 | 1.0 | 1.0 | 1.0 | 1.0 |
| | Polyvinyl Alcohol | | 0.5 | 0.5 | 0.5 | 0.5 | 0.5 | 0.5 | 0.5 |
| | Polysaccharide Derivative manufactured by Kao Corporation Trade Name: SPS-S | | 0.1 | 0.1 | 0.1 | 0.1 | 0.1 | 0.1 | 0.1 |
| | Ion-exchanged Water | | balance | balance | balance | balance | balance | balance | balance |
| Strength of Disperse Phase (kPa) (*2) | | | 15 | 3.2 | 172 | 99 | 175 | 1.0 or less | 1.0 or less |
| Melting Point of Disperse Phase (°C.) | | | 41 | 59 | 65 | 61 | 60 | — | 56 |

(*1) Mixture of 2-Ethylhexyl 4-Methoxycinnamate 25.0 mass % and 4-Methoxy-4'-tert-butyldibenzoylmethane 2.5 mass %
(*2) Detection limit of disperse phase strength: 1.0 kPa (Test and Evaluation)
<Compressive-Breaking Stress of Disperse Phase>

As for each of the hydrogel particles of Examples 1 to 5 and Comparative Examples 1 and 2, the compression breaking stress of the solid material of the disperse phase was measured using a digital force gauge (FGX-0.2R manufactured by NIDEC-SHIMPO CORPORATION (minimum measurement load: 2 mN)). The "compression breaking stress" herein means the local maximum value of the load curve. The gauge head was a flat adapter, and the lowering speed of the gauge head was 10 mm/min. The measurement temperature was 25° C.

<Leakage of Zinc Oxide Fine Particles>

As for each of the hydrogel particles of Examples 1 to 5 and Comparative Examples 1 and 2, applicability to sunscreen gel was examined as follows. First, the cosmetic constituents shown in TABLE 2 except for the hydrogel particles were uniformly mixed. Triethanolamine was added to the mixture, which was then regulated to pH 5.5. Thereafter, the hydrogel particles were added to the mixture at the concentration of 10 mass %, whereby a cosmetic product of carboxylvinyl polymer aqueous solution containing the hydrogel particles dispersed therein were prepared.

As for each of the hydrogel particles of Examples 1 to 3 and Comparative Examples 1 and 2, the viscosity and pH of the carboxylvinyl polymer aqueous solution containing the hydrogel particles dispersed therein were measured with time. As for Examples 4 and 5, pH of the carboxylvinyl polymer aqueous solution containing the hydrogel particles dispersed therein was measured with time. It should be noted that the viscosity was measured at 50° C. using a Brookfield viscometer.

TABLE 2

| Cosmetic Constituents (mass %) | Acrylic Acid Copolymer manufactured by Nikko Chemicals Co., Ltd. Trade Name: Carbopol ETD2020 | 0.3 |
|---|---|---|
| | Acrylic Acid/Alkyl Methacrylate Copolymer manufactured by Nikko Chemicals Co., Ltd. Trade Name: PEMULEN TR-2 | 0.2 |
| | Methylparaben | 0.2 |
| | Ethanol | 15.0 |
| | Purified Water | balance |
| | Hydrogel Particles | 10.0 |

(Results of Test and Evaluation)

The measurement results of the compression breaking stress of the disperse phase portions are shown in TABLE 1.

Referring to TABLE 1, in Examples 1 to 5, the compression breaking stress of the disperse phase portions was 2.0 kPa or more, the disperse phase portions was solid phase, and the zinc oxide fine particles dispersed in the liquid oil were fixed in the disperse phase portions. In Comparative Examples 1 and 2, the compression breaking stress of the disperse phase portions was less than 2.0 kPa. Thus, it is estimated that the zinc oxide fine particles dispersed in the liquid oil were not sufficiently fixed in the disperse phase portions.

The results of measurements with time of the viscosity and pH are shown in TABLE 3 and TABLE 4.

TABLE 3

| | Viscosity (mPa · s, 50° C.) | | | |
|---|---|---|---|---|
| | Initial Viscosity | 1 day later | 3 days later | 7 days later |
| Example 1 | 7020 | 6380 | 3040 | — |
| Example 2 | 7200 | — | 6520 | 4000 |
| Example 3 | 7040 | 7000 | 6900 | 6920 |
| Example 4 | — | — | — | — |
| Example 5 | — | — | — | — |
| Comparative 1 | 7220 | 260 | 20 | — |
| Comparative 2 | 7480 | 120 | — | — |

TABLE 4

| | pH (50° C.) | | | |
|---|---|---|---|---|
| | Initial pH | 1 day later | 3 days later | 7 days later |
| Example 1 | 5.5 | 6.9 | 7.4 | — |
| Example 2 | 5.5 | — | 6.1 | 6.7 |
| Example 3 | 5.5 | 5.7 | 5.6 | 5.7 |
| Example 4 | 5.5 | 5.6 | 5.6 | 5.6 |
| Example 5 | 5.5 | 5.6 | 5.6 | 5.6 |
| Comparative 1 | 5.5 | 7.7 | 7.8 | — |
| Comparative 2 | 5.5 | 7.7 | — | — |

Referring to TABLE 3 and TABLE 4, in Examples 1 to 3, the viscosity of the carboxylvinyl polymer aqueous solution containing the hydrogel particles dispersed therein was maintained high over time, and the stability of pH over time was excellent. In Comparative Examples 1 and 2, the viscosity of the carboxylvinyl polymer aqueous solution containing the hydrogel particles dispersed therein significantly decreased over time, and the pH value significantly increased. It is estimated that, in Examples 1 to 3, the zinc oxide fine particles were fixed in the disperse phase portions, so that leakage of the zinc oxide fine particles into the carboxylvinyl polymer aqueous solution was suppressed, and therefore, the gel structure of the carboxylvinyl polymer aqueous solution, which is the disperse medium of the hydrogel particles, was maintained. In Comparative Examples 1 and 2, it is estimated that, the zinc oxide fine particles were not sufficiently fixed in the disperse phase portions, so that leakage of the zinc oxide fine particles into the carboxylvinyl polymer aqueous solution, which is the disperse medium of the hydrogel particles, occurred.

Although as for Examples 4 and 5 the viscosity was not measured, it is estimated from the results of the measurement of the compression breaking stress and pH of the disperse phase portions over time that the same viscosity measurement results as those of Examples 1 to 3 will be obtained.

INDUSTRIAL APPLICABILITY

The present invention is useful for hydrogel particles applicable to, for example, cosmetic products, quasi drugs, etc.

The invention claimed is:

1. A hydrogel particle, comprising
(A) a continuous phase portion of non-crosslinked hydrogel; and
(B) a disperse phase portion dispersed in said continuous phase portion,
wherein said disperse phase portion is a solid phase and said dispersed phase portion comprises:
(a) an oil component which comprises behenyl alcohol and a liquid oil whose melting point is lower than 35° C.; and
(b) particles of zinc oxide, wherein
a content of the particles of zinc oxide in the disperse phase portion is 10 to 60 mass %
a content of liquid oil in the oil component is 20 to 90 mass %, and
a content of behenyl alcohol in the oil component is 10 to 80 mass %.

2. The hydrogel particle of claim 1, wherein the oil component further comprises solid isoparaffin.

3. The hydrogel particle of claim 1, wherein the liquid oil comprises silicone.

4. The hydrogel particle of claim 1, wherein the volume-average particle diameter of the hydrogel particle is 10 to 10000 μm.

5. The hydrogel particle of claim 1, wherein the average particle diameter of a primary particle of the zinc oxide particles is 0.001 to 0.1 μm.

6. The hydrogel particle of claim 1, wherein a content of the dispersed phase portion in the hydrogel particle is 10 to 70 mass %.

7. The hydrogel particle of claim 1, wherein a content of the continuous phase portion in the hydrogel particle is 30 to 80 mass %.

8. The hydrogel particle of claim 1, wherein the non-crosslinked hydrogel is derived from a gel source comprising agar.

9. The hydrogel particle of claim 8, wherein the content of the gel source in the continuous phase portion is 0.1 to 8.0 mass %.

10. A carboxylvinyl polymer aqueous solution comprising hydrogel particles according to claim 1 dispersed therein.

* * * * *